(12) United States Patent
Fan

(10) Patent No.: US 9,295,670 B2
(45) Date of Patent: *Mar. 29, 2016

(54) METHODS FOR TREATING OBSTRUCTIVE SLEEP APNEA

(71) Applicant: Pfantastic Medical Research Institute, LLC, Cresskill, NJ (US)

(72) Inventor: Jian-Qiang Fan, Harrington Park, NJ (US)

(73) Assignee: PFANTASTIC MEDICAL RESEARCH INSTITUTE, LLC, Cresskill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/269,326

(22) Filed: May 5, 2014

(65) Prior Publication Data

US 2014/0238412 A1 Aug. 28, 2014

Related U.S. Application Data

(63) Continuation of application No. 13/359,692, filed on Jan. 27, 2012, now Pat. No. 8,753,327.

(60) Provisional application No. 61/437,272, filed on Jan. 28, 2011.

(51) Int. Cl.
| | |
|---|---|
| *A61K 31/4412* | (2006.01) |
| *A61K 31/4425* | (2006.01) |
| *A61K 45/06* | (2006.01) |
| *A61F 5/56* | (2006.01) |
| *A61M 16/00* | (2006.01) |

(52) U.S. Cl.
CPC ............ *A61K 31/4412* (2013.01); *A61F 5/566* (2013.01); *A61K 31/4425* (2013.01); *A61K 45/06* (2013.01); *A61M 16/0057* (2013.01)

(58) Field of Classification Search
CPC ....... A61K 31/4425; A61F 5/56; A61F 5/566; A61F 5/08; A61M 31/002
See application file for complete search history.

(56) References Cited

U.S. PATENT DOCUMENTS

| | | | |
|---|---|---|---|
| 5,399,403 A | 3/1995 | Instance | |
| 6,034,117 A | 3/2000 | Hedner et al. | |
| 8,753,327 B2 * | 6/2014 | Fan ............................. | 604/500 |
| 2008/0066739 A1 | 3/2008 | LeMahieu et al. | |
| 2008/0261931 A1 * | 10/2008 | Hedner et al. ................ | 514/171 |

FOREIGN PATENT DOCUMENTS

| | | |
|---|---|---|
| EP | 0 923 370 B1 | 11/2005 |
| WO | WO 97/22339 | 6/1997 |

OTHER PUBLICATIONS

Almog et al., *Isr. J. Med. Sci.* 27: 659-63 (1991).
(Continued)

*Primary Examiner* — Laura Bouchelle
(74) *Attorney, Agent, or Firm* — RatnerPrestia

(57) ABSTRACT

The present invention relates to methods for treating obstructive sleep apnea (OSA), alleviating a negative OSA symptom, reducing snoring, or improving quality of life in a subject, comprising administering to the subject an effective amount of a pharmaceutical composition comprising pyridostigmine before sleep. Also provided are related medicaments as well as methods for preparing the medicaments.

20 Claims, 10 Drawing Sheets

(56) References Cited

OTHER PUBLICATIONS

Aquilonius et al., *J Neurol Neurosurg Psychiatry.* 46:929-35 (1983).
Aquilonius et al., *Eur J Clin Pharmacol.* 18:423-8 (1980) (Abstract).
Banno & Kryger, *Sleep Med.* 8, 400-26 (2007).
Banno et al., *J Clin Sleep Med.* 1, 364-6 (2005).
Collop et al., *J Clin Sleep Med.* 3, 737-47 (2007).
Davison et al., Journal of Neurology, Neurosurgery, and Psychiatry 44:1141-1145 (1981).
Epstein et al., *J Clin Sleep Med.* 5, 263-76 (2009).
Fleisher et al., *J Oral Maxillofac Surg.* 65, 2056-68 (2007).
Hedner et al., *Sleep Med Rev.* 12:33-47 (2008).
Hedner et al., *Am J Respir Crit Care Med.* 168:1246-51 (2003).
Hetherington and Losek, *Pediatr Emerg Care* 21: 546-8 (2005).
Huang et al., *Drug Dev Ind Pharm.* 33:1183-91 (2007).
Huang et al., *Drug Dev Ind Pharm.* 33:403-16 (2007).
Jayaraman et al., Ther Adv Respir Dis. 2:375-86 (2008).
Kushida et al., *Sleep.* 28:499-521 (2005).
Levy, *J Pharm Sci* 56:928-29 (1967).
Jean-Louis et al., Expert Rev Cardiovasc Ther. 8:995-1005 (2010).
Mansfield et al., *Am J Respir Crit Care Med.* 169:361-6 (2004).
Mestinon (pyridostigmine bromide syrup), *Valeant® Pharmaceuticals North America*, 07-3012-EX-00 pp. 1-9 (2008).
Milner-Brown et al., Annals NY Academy Sci 505:838-41 (1987).
Milner-Brown et al., *Neurology.* 37:800-3 (1987).
Moraes et al., *Chest.* 133:677-83 (2008).
Package insert for MESTINON® (pyridostigmine bromide) syrup, tablets and TIMESPAN® Tablets, 2 pages (2001).
Riches, *Lancet* 1: 540-41 (1954).
Roberts and Denton, *Eur J Clin Pharmacol.* 18:175-83 (1980).
Schmidt and Roholt, *Acta Pathologica er Microbiol Scandinacixa.* 68: 396-400 (1966).
Shyu et al. *Clin Pharmacokinet.* 25: 237-42 (1993).
Swartz and Sidell, *Clin Pharmacol Ther.* 14: 83-89 (1973).
Tregear et al, *J Clin Sleep Med.* 5:573-81 (2009).
Wagner, Fundamentals of clinical pharmacokinetics. Chap. 11. Effect of normal and pathologic physiology on pharmacokinetics, by Drug Intelligence Publications, Hamilton, pp. 359-395 (1975).
Weaver et al., *Proc Am Thorac Soc.* 5:173-8 (2008).
Yamamoto et al., *Journal of Pharmacokinetics and Biopharmaceutics*, 24(4):327-48 (1996).
Young et al. *N. Engl J Med.* 328:1230-5 (1993).
Young et al., *Am J Respir Crit Care Med.* 165:1217-39 (2002).
First Office Action from the European Patent Office in European Patent Applicantion 12739245.4 dated Aug. 10, 2015.
Iber et al., AASM Manual for Scoring Sleep, pp. 3-59 (2007).
Epstein et al., *Journal of Clinical Sleep Medicine* 5(3):263-76 (2009).

* cited by examiner

*, P value < 0.01; , 0.01 < P value < 0.05; *, P value > 0.05

METHODS FOR TREATING OBSTRUCTIVE SLEEP APNEA

RELATED APPLICATIONS

This application is a continuation application of U.S. patent application Ser. No. 13/359,692, filed Jan. 27, 2012, allowed, which claims the benefit of U.S. Provisional Application No. 61/437,272, filed on Jan. 28, 2011, the contents of each of which are incorporated by reference herein, in their entireties and for all purposes.

FIELD OF THE INVENTION

The invention relates generally to a method for treating obstructive sleep apnea (OSA) or to other related symptoms in a subject in need thereof, related medicaments, pharmaceutical compositions, and methods for preparing the medicaments.

BACKGROUND OF THE INVENTION

Obstructive sleep apnea (OSA) is a serious, potentially life-threatening highly prevalent chronic disorder. It is an important and unresolved public health care problem because of its role in the development of cardiovascular events, negative impact on quality of life, and as a cause of traffic accidents. The signs, symptoms and consequences of OSA are direct results of repetitive episodes of airflow cessation (i.e., apnea) or reduction (i.e., hypopnea) due to repetitive collapse of the upper airway. Reduced ventilation during sleep causes repetitive episodes of hypoxemia, increased arterial $CO_2$, and decreased arterial $O_2$. A correlation has been clearly established that patients with OSA are often associated with cardiovascular diseases (e.g., systemic hypertension, pulmonary hypertension, arrhythmia, and heart failure), neuropsychiatric diseases (e.g., cognitive dysfunction caused by excessive daytime sleepiness, lowered quality of life caused by snoring, fragmented sleep due to arousals, and depression), and metabolic diseases (e.g., obesity, diabetes mellitus, and insulin resistance). OSA affects at least 2% to 4% of the adult population and is increasingly recognized by the public. A more recent report estimates that OSA affects approximately 5% of adults; however, the prevalence of OSA may be increasing because of recent obesity trends.

Continuous positive airway pressure (CPAP) is currently the first-line standard of care for treating OSA. By delivering a fan generated airflow, CPAP maintains airway patency by creating a "pneumatic splint." In most patients, CPAP dramatically reduces or eliminates apnea and hypopnea episodes. However, the effectiveness of CPAP depends directly on patients' utilization of the machine and mask. Only half of those individuals who accept CPAP are still using it at the end of one year, and even fewer use it to the extent prescribed. Surgical treatment has also been used to treat OSA, and surgical techniques include stage I surgery (e.g., nasal surgery, uvulopalatopharyngoplasty, and base of tongue surgery) and stage II surgery (e.g., maxillomandibular advancement). The goal of surgery is to provide site-specific treatment to increase airway size and decrease airway resistance, thereby reducing work of breathing. A successful site-specific airway reconstruction often depends on the site of obstruction which is unique to each patient and is not consistent within patients. These mechanical and surgical treatments are inconvenient and often intrusive to patients.

Various pharmaceutical agents have been trialed for the treatment for OSA, but none has been found to be adequately effective. Hedner and Kraiczi initially claimed treatment of snoring, sleep apnea and other forms of sleep-disordered breathing with an acetylcholinesterase inhibitor (CEI) based on a clinical study of patients with moderate to severe OSA treated with continuous intravenous infusion of physostigmine salicylate at 12 µg/min/kg for a period of 7 hours, and provided a list of other CEIs, including pyridostigmine, particularly useful for the treatment (U.S. Pat. No. 6,034,117). After publishing subsequent reports on similar results in patients treated with continuous intravenous infusion of physostigmine at 0.12 µg/min/kg for a period of 7 hours or donepezil, Hedner disclosed that more recent unpublished data did not fully support the initial promising findings and concluded that the therapeutic potential of CEIs in OSA remained to be clarified (Hedner et al. (2008), *Sleep Medicine Reviews* 12:33-47).

Therefore, there remains a need for a convenient, less intrusive and effective OSA treatment, especially a potent therapeutic agent that can be easily administered.

SUMMARY OF THE INVENTION

The present invention relates to the use of pyridostigmine (PYD) in treating obstructive sleep apnea (OSA) or other related symptoms and pharmaceutical compositions or medicaments comprising PYD, preferably using a specific dosage form and dosage amount.

A method for treating obstructive sleep apnea (OSA) in a subject in need thereof is provided. The method comprises administering to the subject an effective amount of a pharmaceutical composition comprising pyridostigmine before sleep. Upon treatment, apnea, hypopnea, snoring, or low oxygen saturation events may be reduced, and sleep quality or daytime quality of life may be improved.

A method for alleviating a negative symptom of obstructive sleep apnea (OSA) in a subject is provided. The method comprises administering to the subject an effective amount of a pharmaceutical composition comprising pyridostigmine before sleep. The negative symptom may be apnea, hypopnea, snoring, low oxygen saturation, frequent arousal events, poor sleep quality, daytime sleepiness, or frequent loss of memory.

A method for reducing snoring in a subject suffering from obstructive sleep apnea (OSA) is provided. The method comprises administering to the subject an effective amount of a pharmaceutical composition comprising pyridostigmine before sleep.

A method for improving quality of life of a subject suffering from obstructive sleep apnea (OSA) is provided. The method comprises administering to the subject an effective amount of a pharmaceutical composition comprising pyridostigmine before sleep. The improving quality of life may be improving sleep quality, reducing daytime sleepiness, or increasing memory.

In a method according to the present invention, the effective amount of the pharmaceutical composition may be selected to provide a target serum concentration of pyridostigmine in the subject in the range of about 2-150 ng/ml, 3-60 ng/ml, 3-45 ng/ml, 3-30 ng/ml, or 3-15 ng/ml for at least one, three, six or seven hours.

The effective amount of the pharmaceutical composition in these methods may be about 30-360 mg, 30-180 mg, or 30-120 mg pyridostigmine, preferably in an orally ingestible dosage form. The amount of pyridostigmine in the composition may be about 30, 60, 90, 120, 180 or 360 mg.

The pharmaceutical composition may be administered to the subject within about 2 hours, 1 hour, 30 minutes, 15 minutes or 5 minutes before sleep.

The pharmaceutical composition may be administered to the subject in a single dose or multiple doses.

The pharmaceutical composition may further comprise a pharmaceutically acceptable carrier or diluent.

The pharmaceutical composition may be administered to the subject in an oral dosage form, preferably for gastrointestinal adsorption.

The pharmaceutical composition may be administered to the subject in a dosage form for controlled release of pyridostigmine.

A method according to the present invention may further comprise providing the subject a mechanical treatment. The mechanical treatment comprises the use of continuous positive airway pressure (CPAP) devices, mandibular repositioning appliances (MRA) or tongue retaining devices.

A method according to the present invention may further comprise administering to the subject an effective amount of a deep sleep promoting agent. The deep sleep promoting agent may be selected from the group consisting of antidepressants, selective serotonin reuptake inhibitors, bensodiazepines, cyclopyrrolones and antihistamine.

The subject may be a human, preferably an OSA patient. The subject may suffer mild, moderate or severe OSA. The subject may be male or female. The subject may be obese or not obese.

The subject may have suffered a cardiovascular disease. The cardiovascular disease may be systemic hypertension, pulmonary hypertension, arrhythmia or heart failure.

The subject may have suffered a neuropsychiatric disease. The neuropsychiatric disease may be cognitive dysfunction caused by excessive daytime sleepiness, lowered quality of life caused by snoring, fragmented sleep due to arousals, or depression.

The subject may have suffered a metabolic disease. The metabolic disease may be obesity, diabetes mellitus or insulin resistance.

The subject may have suffered a congestive heart failure, atrial fibrillation, refractory hypertension, type 2 diabetes, stroke, nocturnal dysrhymias and/or pulmonary hypertension. The subject may have been evaluated for bariatric surgery.

For all of the methods described herein, a medicament comprising an effective amount of pyridostigmine is provided.

The medicament is useful for treating obstructive sleep apnea (OSA). The medicament may be useful for reducing apnea, hypopnea, snoring, or low oxygen saturation events and/or improving sleep quality or daytime quality of life.

The medicament is also useful for alleviating a negative symptom of obstructive sleep apnea (OSA). The negative symptom may be any one or more of apnea, hypopnea, snoring, low oxygen saturation, frequent arousal events, poor sleep quality, daytime sleepiness, and frequent loss of memory.

The medicament is also useful for reducing snoring and improving quality of life. The latter may include improving sleep quality, reducing daytime sleepiness, or increasing memory.

The effective amount of the medicament may be selected to provide a target serum concentration of pyridostigmine in a subject in the range of about 2-150 ng/ml, 3-60 ng/ml, 3-45 ng/ml, 3-30 ng/ml, or 3-15 ng/ml for at least one, three, six or seven hours.

A medicament according to the present invention may comprise about 30-360 mg, 30-180 mg, or 30-120 mg pyridostigmine. Individual dosage forms of the medicament may comprise about 30, 60, 90, 120, 180, or 360 mg pyridostigmine.

A medicament according to the present invention may further comprise a pharmaceutically acceptable carrier or diluent.

A method for preparing a medicament useful for treating obstructive sleep apnea (OSA) is provided. The method comprises admixing pyridostigmine with a pharmaceutically acceptable carrier or diluent. The medicament may be useful for reducing apnea, hypopnea, snoring, or low oxygen saturation events, and/or improving sleep quality or daytime quality of life.

A method for preparing a medicament useful for alleviating a negative symptom of obstructive sleep apnea (OSA) is provided. The method comprises admixing pyridostigmine with a pharmaceutically acceptable carrier or diluent. The negative symptom is selected from the group consisting of apnea, hypopnea, snoring, low oxygen saturation, frequent arousal events, poor sleep quality, daytime sleepiness, and frequent loss of memory.

A method for preparing a medicament useful for reducing snoring is provided. The method comprises admixing pyridostigmine with a pharmaceutically acceptable carrier or diluent.

A method for preparing a medicament useful for improving quality of life is provided. The method comprises admixing pyridostigmine with a pharmaceutically acceptable carrier or diluent. The medicament may be useful for improving sleep quality, reducing daytime sleepiness, or increasing memory.

In a method for preparing a medicament according to the present invention, the medicament may comprise about 30-360 mg, 30-180 mg or 30-120 mg pyridostigmine. The amount of pyridostigmine may be about 30, 60, 90, 120, 180, or 360 mg.

DETAILED DESCRIPTION OF THE INVENTION

Figure 1:
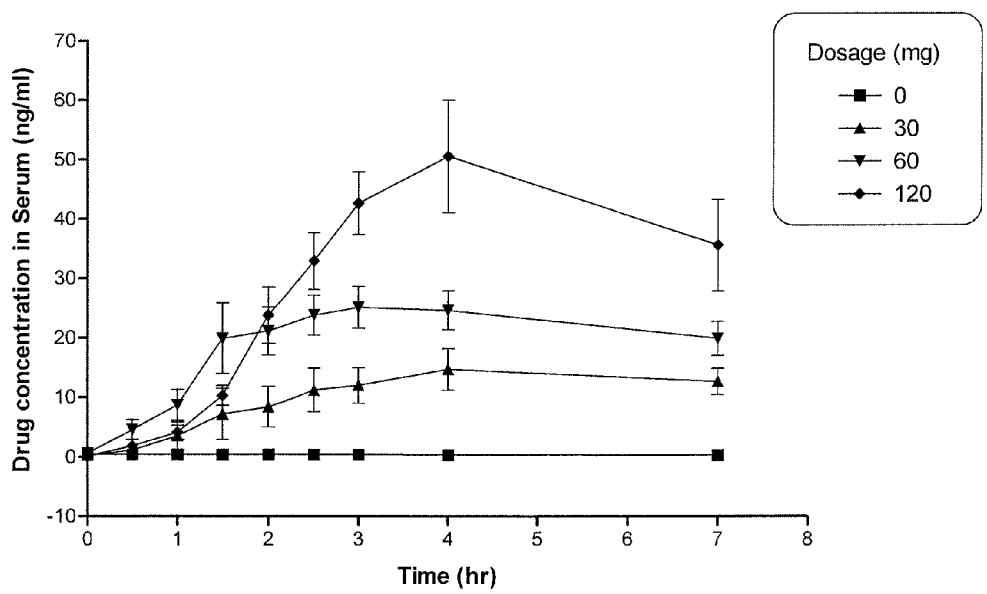
FIG. 1 shows average serum drug concentrations in OSA patients after pyridostigmine treatment.

The present invention is based on the discovery that pyridostigmine (PYD), an acetylcholinesterase inhibitor, is effective in treating obstructive sleep apnea (OSA). In particular, PYD is effective in reducing apnea, hypopnea, snoring and low oxygen saturation events, and improving sleep quality and daytime quality of life of OSA patients.

PYD is a parasympathomimetic and a reversible cholinesterase inhibitor. PYD inhibits acetylcholinesterase in the synaptic cleft, thus slowing down the hydrolysis of acetylcholine, which is a neurotransmitter in both the peripheral nervous system (PNS) and central nervous system (CNS). In the peripheral nervous system, when acetylcholine binds to acetylcholine receptors on skeletal muscle fibers, it opens ligand-gated sodium channels in muscle cell membrane. Sodium ions then enter the muscle cell, initiating a sequence of steps that finally produce muscle contraction. PYD is a quaternary carbamate inhibitor of cholinesterase that does not cross the blood-brain barrier. Clinically, PYD bromide is used to treat muscle weakness in people with myasthenia gravis and to combat the effects of curariform drug toxicity. The chemical structure of PYD is shown in Formula I.

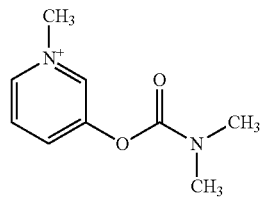

Formula I

The term "pyridostigmine" used herein refers to the compound of Formula I, as well as any other chemically active forms thereof, and pharmaceutically acceptable salts of these compounds.

The term "obstructive sleep apnea (OSA)" used herein refers the occurrence of daytime sleepiness, loud snoring, witnessed breathing interruptions, or awakenings due to gasping or choking in the presence of at least 5 obstructive respiratory events (apneas, hypopneas or respiratory effort related arousals) per hour of sleep.

The term "apnea" used herein refers to suspension of external breathing. Apnea causes airflow cessation in the upper airway of a subject.

The term "hypopnea" used herein refers to overly shallow breathing or an abnormally low respiratory rate. Hypopnea causes airflow reduction in the upper airway of a subject.

The term "snoring" used herein refers to breathing during sleep with a rough hoarse noise due to vibration of respiratory structures.

The term "low oxygen ($O_2$) saturation" used herein refers to a continuous decrease of arterial $O_2$ saturation for greater than 4%, and is expressed as the number of low arterial $O_2$ saturation events per hour.

The term "sleep" used herein refers to a natural state of rest, in which eyes are closed, consciousness is completely or partially lost, and bodily movement or responsiveness to external stimuli is reduced, or, in a clinical study, a period from lights off to a natural wake-up or lights on, whichever is earlier.

The term "sleep quality" used herein refers to the degree of excellence of sleep, which is determined by numerous factors, including total sleep time and feelings about sleep.

The term "daytime quality of life" used herein refers to the degree of excellence of daytime life, which is determined by numerous factors, including energy level, concentration level and sleepiness during daytime, and restoration of impaired cognitive function (e.g., impaired memory).

The term "quality of life" used herein includes both sleep quality and daytime quality of life.

The term "a negative symptom of obstructive sleep apnea (OSA)" used herein refers to a symptom of OSA having an adverse impact on health or life. Examples of negative OSA symptoms include apnea, hypopnea, snoring, low oxygen saturation, frequent arousal events, poor sleep quality, daytime sleepiness, and frequent loss of memory.

The term "obesity" or "being obese" used herein refers to a condition of excess body fat accumulated to the extent that it may have an adverse effect on health, leading to reduced life expectancy and/or increased health problems. People having a body mass index (BMI) greater than 30 kg/m$^2$ are generally considered obese.

The term "subject" used herein refers to a mammal, preferably a human, more preferably an OSA patient, most preferably a high-risk OSA patient. The subject may be male or female.

The subject may have suffered a cardiovascular disease, a neuropsychiatric disease or a metabolic disease. A cardiovascular disease may be systemic hypertension, pulmonary hypertension, arrhythmia or heart failure. A neuropsychiatric disease may be cognitive dysfunction caused by excessive daytime sleepiness, lowered quality of life caused by snoring, fragmented sleep due to arousals, or depression. A metabolic disease may be obesity, diabetes mellitus or insulin resistance.

High-risk OSA patients include those who are obese, those with congestive heart failure, atrial fibrillation, refractory hypertension, type 2 diabetes, stroke, nocturnal dysrhythmias and/or pulmonary hypertension, high-risk driving populations (e.g., commercial truck and taxi drivers), and those being evaluated for bariatric surgery.

The term "about" as used herein when referring to a measurable value such as an amount, a percentage, and the like, is meant to encompass variations of +20% or ±10%, more preferably ±5%, even more preferably ±1%, and still more preferably ±0.1% from the specified value, as such variations are appropriate.

OSA diagnosis may be performed with a history and physical examination and objective testing which involve in-laboratory polysomnography (PSG) or portable monitors (PM). PSG is routinely indicated for diagnosis of sleep related breathing disorders. The use of PSG for OSA evaluation requires recording physiologic signals, including electroencephalogram (EEG), electrooculogram (EOG), chin electromyogram (EMG), airflow, oxygen saturation, respiratory effort, electrocardiogram (ECG), and heart rate. Additional parameters may include body position and leg EMG derivations. Anterior tibialis EMG is useful to assist in detecting movement arousals and may have an added benefit of assessing periodic limb movements, which coexist with sleep related breathing disorders in many patients. PMs may be used to diagnose OSA when utilized as a part of a comprehensive sleep evaluation in subjects with a high risk of moderate to severe OSA. A PM may, at a minimum, record airflow, respiratory effort, and blood oxygenation. Biosensors used to monitor these parameters for in-laboratory PSG are recommended for use in PMs. They may include an oronasal thermal sensor to detect apneas, a nasal pressure transducer to measure hypopneas, oximetry, and, ideally, calibrated or uncalibrated inductance plethysmography for respiratory effort. The parameters, settings, filters, technical specifications, sleep stage scoring and event scoring may be determined in accordance with the AASM Manual for the Scoring of Sleep and Associated Events.

Obstructive events include apnea, hypopnea and respiratory event related arousals (RERAs). RERAs are arousals from sleep that do not technically meet the definitions of apneas or hypopneas, but do disrupt sleep. The frequency of obstructive events is reported as an apnea-hypopnea index (AHI), which is the number of apnea or hypopnea events per hour, or respiratory disturbance index (RDI), which is the number of RERAs per hour. OSA diagnosis is made if the number of obstructive events on PSG is greater than 15 events per hour or greater than 5 per hour in a patient who reports at least one of the following: unintentional sleep episodes during wakefulness; daytime sleepiness; unrefreshing sleep; fatigue; insomnia; waking up breath holding, gasping, or choking; or the bed partner describing loud snoring, breathing interruptions, or both during the patient's sleep. OSA severity is defined as mild for AHI between 5 and 15, moderate for AHI between 15 and 30, and severe for AHI greater than 30.

The present invention provides various methods, including a method for treating OSA in a subject in need thereof, a method for alleviating a negative symptom of a subject suffering from OSA, a method for reducing snoring in a subject suffering from OSA, and a method for improving quality of life of a subject suffering from OSA. These methods comprise administering to the subject an effective amount of a pharmaceutical composition comprising pyridostigmine before sleep. Where a subject is treated for OSA, apnea, hypopnea, snoring, or low oxygen saturation events may be reduced, and sleep quality or daytime quality of life may be improved.

An "effective amount" refers to an amount of pyridostigmine or a pharmaceutical composition comprising pyridostigmine required to achieve a stated goal (e.g., treating OSA, alleviating a negative OSA symptom, reducing snoring, and improving quality of life). The effective amount will vary depending upon the stated goals (treating, alleviating, reducing or improving), the physical characteristics of the subject, the severity of OSA, existence of related or unrelated medical conditions, the nature of the composition, the means to administering the drug to the subject, and the administration route. A specific dose for a given subject is generally set by the judgment of a physician.

The effective amount of the pharmaceutical compositions according to the present invention may be selected to provide a target serum concentration of pyridostigmine in the subject in the range of about 2-150 ng/ml, preferably about 3-60 ng/ml, 3-45 ng/ml, 3-30 ng/ml, or 3-15 ng/ml, for at least one hour, preferably three hours, more preferably six hours, most preferably seven hours.

The pharmaceutical compositions may comprise about 30-360 mg, preferably 30-180 mg, more preferably about 30-120 mg, pyridostigmine. For example, the pharmaceutical compositions may comprise about 30 mg, 60 mg, 90 mg, 120 mg, 180 mg or 360 mg. They may further comprise a pharmaceutically acceptable carrier, diluent and/or excipient. Suitable carriers, diluents and excipients are known in the art.

PYD has a short elimination half-life of approximately 1.78 hours. To maintain a maximum therapeutic effect for OSA, a sustained serum concentration at an appropriate range during the sleep period would be desirable. This may be achieved by a pharmaceutical composition from which pyridostigmine is released in a controlled manner over a period of time. For example, a dosage form may be prepared to comprise a core of controlled-released formulation covered by a layer of immediate-released formulation. The immediate release formulation provides a target drug serum concentration quickly while the controlled-release formulation maintains a target drug serum concentration for a duration (e.g., at least 1, 2, 3, 6 and 7 hours), preferably at least 3-4 hours, more preferably 6-7 hours. The controlled-released formulation of PYD may be developed according to methods previously described. The controlled release PYD formulation may comprise about 30-360 mg (e.g., about 30, 60, 90. 120, 180 and 360 mg) of PYD.

The pharmaceutical composition may be administered to the subject before sleep, for example, within about 2 hours, 1 hour, 30 minutes, 15 minutes or 5 minutes before sleep. The administration may be carried out in one or multiple doses, preferably a single dose.

Pharmaceutical compositions may be formulated, for example, for an oral, sublingual, intranasal, intraocular, rectal, transdermal, mucosal, topical or parenteral administration. Parental administration include intradermal, subcutaneous, intramuscular (i.m.), intravenous (i.v.), intraperitoneal (i.p.), intra-arterial, intramedullary, intracardiac, intra-articular (joint), intrasynovial (joint fluid area), intracranial, intraspinal, and intrathecal (spinal fluids). Any device suitable for parental injection or infusion can be used. According to the present invention, the pharmaceutical compositions are preferably administered in an oral dosage form, preferably for gastrointestinal adsorption.

The methods according to the present invention may further comprise providing the subject a mechanical treatment. The mechanical treatment preferably treats or improves OSA, and may comprise the use of continuous positive airway pressure (CPAP) devices, mandibular repositioning appliances (MRA) or tongue retaining devices.

Currently, CPAP is a standard care for OSA patients. In order to take full advantage of CPAP, pressure adjustment is important to each patient, whereas a severe patient generally requires a higher operating pressure. PYD can be used in conjunction with CPAP to reduce the pressure. Patients may gain greater therapeutic effects in a combination of using PYD with CPAP.

Custom made oral appliances may improve upper airway patency during sleep by enlarging the upper airway and/or by decreasing upper airway collapsibility (e.g., improving upper airway muscle tone). Mandibular repositioning appliances (MRA) cover the upper and lower teeth and hold the mandible in an advanced position with respect to the resting position. Tongue retaining devices (TRD) hold only the tongue in a forward position with respect to the resting position, without mandibular repositioning. A combination of PYD treatment with these oral appliances may achieve higher therapeutic effects.

PYD may be administered to the subject with one or more other active agents. Preferably, the other active agents do not reduce or eliminate the effectiveness of PYD. For example, the subjects may further be treated with an effective amount of a deep sleep promoting agent. Examples of the deep sleep promoting agents include anti-depressants, selective serotonin reuptake inhibitors, bensodiazepines, cyclopyrrolones and antihistamine. The PYD composition and the deep sleep promoting agent composition may be administered to the subjects concurrently or sequentially.

In some embodiments, medicaments comprise an effective amount of pyridostigmine is provided. They are useful for treating obstructive sleep apnea (OSA), including reducing apnea, hypopnea, snoring, or low oxygen saturation events, and improving sleep quality or daytime quality of life; for alleviating a negative symptom of obstructive sleep apnea (OSA), which negative symptom is selected from the group consisting of apnea, hypopnea, snoring, low oxygen saturation, frequent arousal events, poor sleep quality, daytime sleepiness, and frequent loss of memory; for reducing snoring; for improving quality of life, including improving sleep quality, reducing daytime sleepiness, or increasing memory.

The effective amount of the medicaments may be selected to provide a target serum concentration of pyridostigmine in the subject in the range of about 2-150 ng/ml, 3-60 ng/ml, 3-45 ng/ml, 3-30 ng/ml, or 3-15 ng/ml for at least one, three, six or seven hours. The medicaments may further comprise a pharmaceutically acceptable carrier or diluent.

The medicaments may comprise pyridostigmine in the range of about 30-360 mg, 30-180 mg or 30-120 mg, for example, about 30, 60, 90, 120, 180, or 360 mg. The medicaments may further comprise a pharmaceutically acceptable carrier or diluent.

In some other embodiments, methods for preparing the medicaments according to the present invention are provided. The preparation methods comprise admixing pyridostigmine with a pharmaceutically acceptable carrier or diluent.

EXAMPLE 1

Determination of Effective Serum Concentrations of PYD in OSA Patients

A randomized, double-blind, placebo-controlled, cross-over study with PYD was undertaken in 12 patients with moderate to severe OSA. PYD was prepared by grinding pyridostigmine bromide pills manufactured by Sunve Pharmaceutical Co., LTD., Shanghai, China and recapsulated into hard shell capsules. PYD bromide at 30 mg, 60 mg, 120 mg, or placebo was orally administered to patients before sleep each night for a total of four continuous nights. Lights went out within 5 min after the administration. Blood was drawn at 0, 0.5, 1, 1.5, 2, 2.5, 3, 4 and 7 hours after the administration, and serum drug concentrations were determined by a LC-MS method after proper pre-treatment of the blood samples. Patients were monitored by either a PSG or a PM throughout the nights.

The serum drug concentrations in the patients are shown in FIG. 1. The peak serum drug concentration was found between 3-4 hours. The patients responded to the drug positively when the serum drug concentrations were between 2-150 ng/ml, particularly between 3-60 ng/ml. The positive responses included reduction of AHI and apnea index (AI, number of apnea event per hour), reduction of total apnea/hypopnea time, reduction of snoring, and increase in minimum oxygen saturation in blood.

Figure 2:
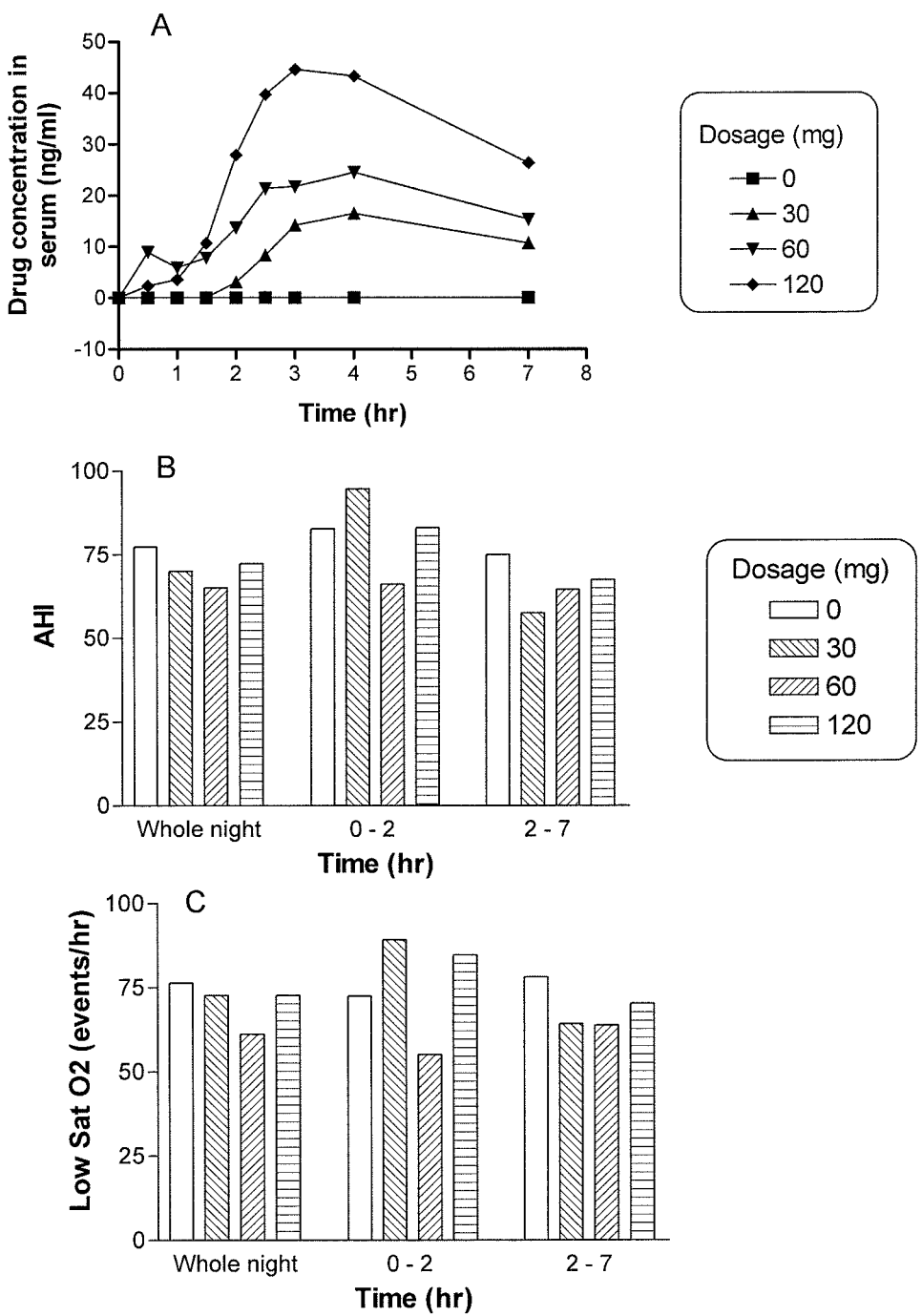
FIG. 2A-C show (A) serum drug concentrations, (B) apnea-hypopnea index (AHI), and (C) low saturated oxygen events in an OSA patient after pyridostigmine treatment.

FIG. 2 shows the data from one patient who was monitored by a PSG for all four nights. The serum drug concentrations in this patient were found to be approximately 3-45 ng/ml.

While AHI and events of low $O_2$ saturation were largely not changed between 0-2 hours after lights off, they were substantially improved between 2-7 hours. Comparing with the placebo, AHIs obtained in the three treatment nights were reduced 11-23%, and the events of low blood $O_2$ saturation were reduced 10-18%.

No serious adverse reaction was reported during the study, although stomach upset and mild muscle cramp were reported in patients treated with the highest dose.

These results indicate that PYD is effective in treating OSA patients and reducing AHI and low blood $O_2$ saturation events, for example, when serum PYD concentrations reach to 2-150 ng/ml.

EXAMPLE 2

Evaluation of the Efficacy and Safety of PYD in Subjects with OSA

A double-blind, randomized, cross-over, placebo-controlled study was conducted to evaluate the efficacy and safety of PYD in 6 diagnosed OSA patients. The study consists of a one-day acclimatization period followed immediately by a 2-day double-blind treatment period when patients received either 90 mg PYD bromide in hard shell capsules or a matching placebo before sleep with a light snack. All patients were required to maintain in a supine position throughout of the night, as OSA is most severe when patients is on their back. In such a way, the results are expected to be more conservative in judging therapeutic effects of the drug. Lights were turned off within 5 min after the administration of the drug. The patients were monitored by a PSG. Apnea, hypopnea, snoring, blood $O_2$ saturation were monitored, recorded, and scored. Sleep questionnaires were taken everyday after sleep to evaluate the impact on the sleep satisfaction and at evening to evaluate the quality of life during the daytime. Safety of the drug was also monitored and evaluated.

Six male patients with mild to moderate OSA were enrolled into the study (Table 1). Compared with the placebo night, AHI, AI, apnea/hypopnea time, events of low $O_2$ saturation, and number of snoring on the treatment night were reduced without statistical significance (i.e., p value>0.05) between 0-2 hours, but with statistical significance between 2-7 hours after lights off. Wide variations in reduction of these measurements were observed among patients between 0-2 hours, probably due to variations in absorption and bioavailability in each patient during that period, and suggesting that the corresponding reduction between 2-7 hours was drug dependent because the serum drug concentration is expected to reach an effective level in all patients between 2-7 hours.

TABLE 1

Characteristics of patients enrolled in the study

| Patient # | Age (yr) | BMI (kg/m$^2$) | Neck circumference (cm) | AHI (events/hr) | AI (events/hr) | Low Sat $O_2$ (%) |
|---|---|---|---|---|---|---|
| 1 | 57 | 26.8 | 38 | 26.2 | 21.8 | 75 |
| 2 | 44 | 29.0 | 40 | 15.7 | 4.6 | 87 |
| 3 | 52 | 26.4 | 37 | 19.3 | 14.2 | 75 |
| 4 | 38 | 28.2 | 37 | 16.7 | 12.0 | 86 |
| 5 | 43 | 26.9 | 39 | 15.0 | 6.3 | 80 |
| 6 | 55 | 32.5 | 44 | 22.5 | 3.6 | 83 |
| Mean | 48.2 | 28.3 | 39.2 | 19.2 | 10.4 | 81 |

Average reduction of AHI, AI, apnea/hypopnea time, and number of snoring between 2-7 hours in the treatment night were 28.0% (p value=0.0003), 37.3 (0.0314), 36.4 (0.0133), and 18.8 (0.0041), respectively (Table 2). The reduction of hypopnea index (HI, number of event per hour) and low $O_2$ saturation events during the same period of time were 10.3, and 12.5%, respectively. Less effectiveness on HI was expected, since a substantial alleviation of apnea could cause an increase in hypopnea. The drug was well tolerated by the patients: no serious adverse reaction was reported, although minor stomach upset was found in one patient. These results indicate that a single dose of PYD bromide at 90 mg is therapeutically effective in treating of OSA patients.

TABLE 2

Summary of the drug effects on subjects diagnosed as obstructive sleep apnea patients

| | Time after sleep | | | | | |
|---|---|---|---|---|---|---|
| | 0-2 hr | | | 2-7 hr | | |
| | Placebo | Drug | Reduction (%) | Placebo | Drug | Reduction (%) |
| Apnea/Hypopnea Index (AHI) | 34.1 | 29.6 | 13.1*** | 28.4 | 20.4 | 28.0* |
| Apnea index (AI) | 23.1 | 16.9 | 26.7*** | 18.7 | 11.7 | 37.3** |
| Hypopnea Index (HI) | 10.2 | 12.0 | −17.7*** | 9.7 | 8.7 | 10.3*** |
| Apnea/Hypopnea time (%) | 23.8 | 18.7 | 21.5*** | 22.8 | 14.5 | 36.4** |
| Low Sat $O_2$ (events/hr) | 37.6 | 35.1 | 6.6*** | 28.5 | 24.9 | 12.5*** |
| Snore score (events/hr) | 546 | 528 | 3.3*** | 597 | 485 | 18.8* |

*P value <0.01;
**0.01 < P value < 0.05;
***P value >0.05.

The detailed results are discussed below:

1) AHI

Figure 3:
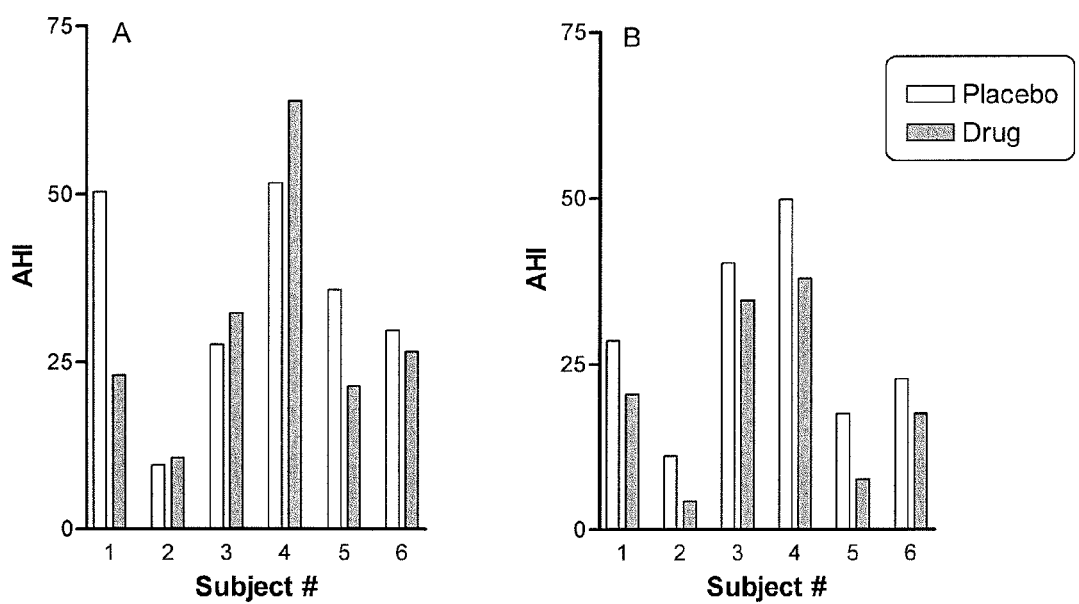
FIGS. 3A-B show apnea-hypopnea index (AHI) in OSA patients (A) 0-2 hours and (B) 2-7 hours after pyridostigmine treatment.

No statistically significant reduction of AHI was found during the sleep period of 0-2 hours (FIG. 3). During the sleep period of 2-7 hours, the reduction of AHI was found in all patients ranging from 13.9% to 61.6% (average of 28.0%). Greater reduction was found in moderate patients compared with severe patients.

2) AI

Figure 4:
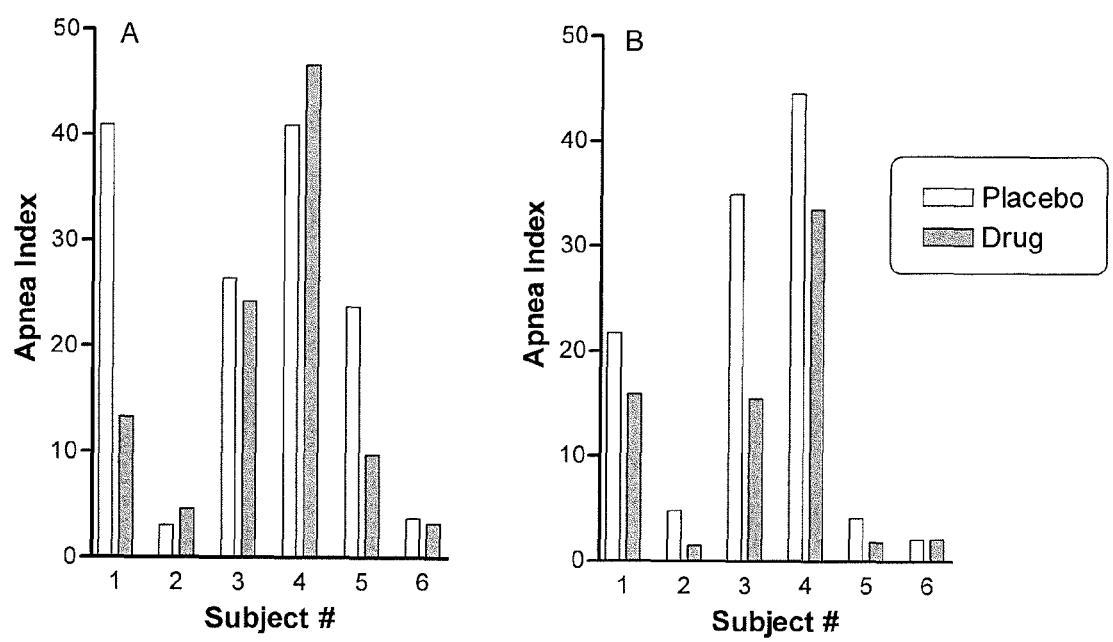
FIGS. 4A-B show apnea index in OSA patients (A) 0-2 hours and (B) 2-7 hours after pyridostigmine treatment.

No statistically significant reduction of AI was found during the sleep period of 0-2 hours (FIG. 4). During the sleep period of 2-7 hours, the reduction of AI was found in 5 patients ranging from 24.7% to 68.8% (average 37.3% in 6 patients). No reduction was found in one patient who had AI of 2.1.

3) Total Apnea/Hypopnea Time

Figure 5:
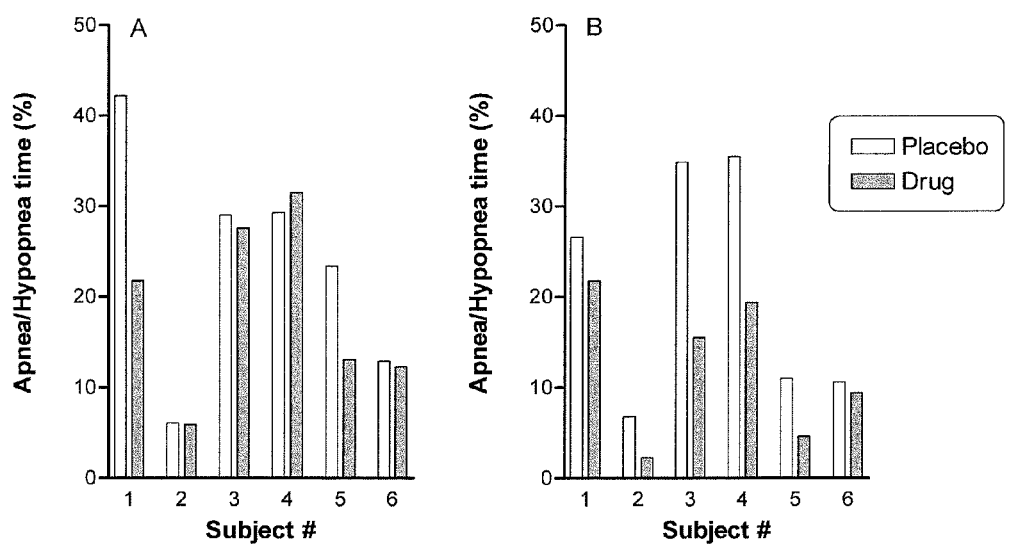
FIGS. 5A-B show apnea/hypopnea time in OSA patients (A) 0-2 hours and (B) 2-7 hours after pyridostigmine treatment.

Total apnea/hypopnea time was expressed as a percentage of the total sleep time that apnea or hypopnea occurred. No statistically significant reduction of total apnea/hypopnea time was found during the sleep period of 0-2 hours (FIG. 5). During the sleep period of 2-7 hours, the reduction of total apnea/hypopnea time was found in all the patients ranging from 11.3% to 66.2% (average 36.4%).

4) Low $O_2$ Saturation

Figure 6:
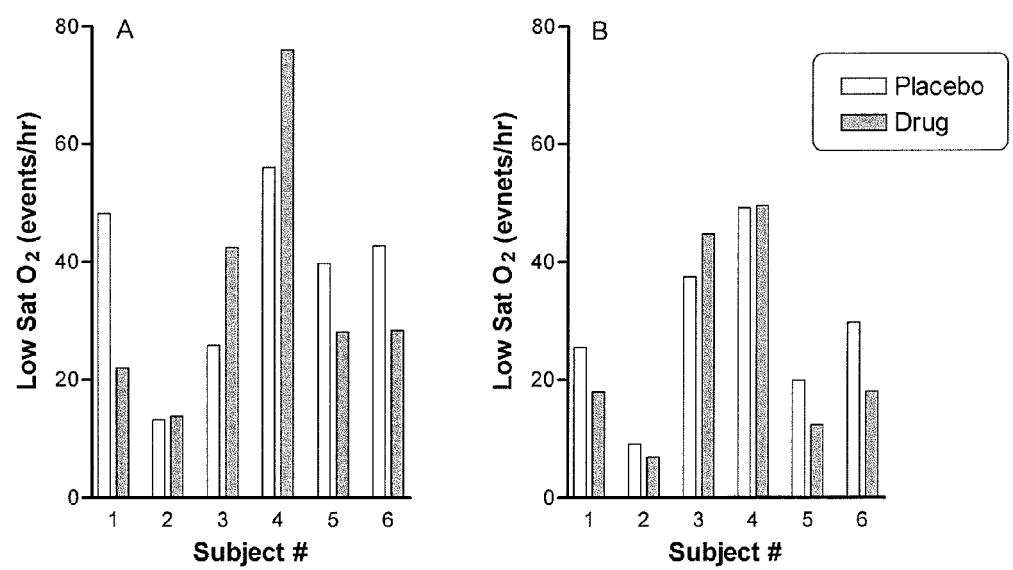
FIGS. 6A-B show low saturated oxygen events in OSA patients (A) 0-2 hours and (B) 2-7 hours after pyridostigmine treatment.

Low $O_2$ saturation was expressed as the number of low $O_2$ saturation event per hour. A low $O_2$ saturation event is characterized as continuous decrease of arterial $O_2$ saturation for greater than 4%. No statistically significant reduction of low $O_2$ saturation was found during the sleep period of 0-2 hours (FIG. 6). During the sleep period of 2-7 hours, the reduction of low $O_2$ saturation was found in 4 patients ranging from 24.2% to 39.4%. No reduction was found in 1 patient, and in patient the number of the event was increased.

5) Snoring

Figure 7:
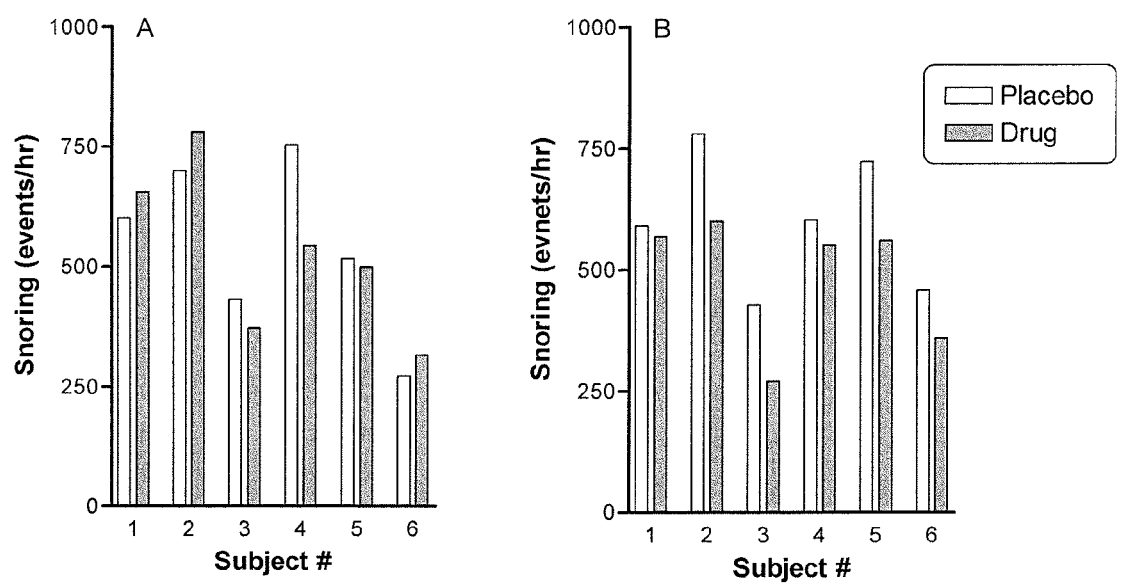
FIGS. 7A-B show snoring events in OSA patients (A) 0-2 hours and (B) 2-7 hours after pyridostigmine treatment.

Snoring was calculated as the number of snoring per hour. No statistically significant reduction of snoring was found during the sleep period of 0-2 hours (FIG. 7). During the sleep period of 2-7 hours, the reduction of snoring was found in all patients ranging from 3.7% to 36.9% (average 18.8%). Snoring in the treatment night was quieter comparing with the placebo night, indicating the drug reduced the noise of snoring. Even in the patient who had 3.7% reduction, snoring in the treatment night was short and high pitched, thus the total snoring time is reduced although the number of snore did not change much.

6) Sleep Quality

Figure 8:
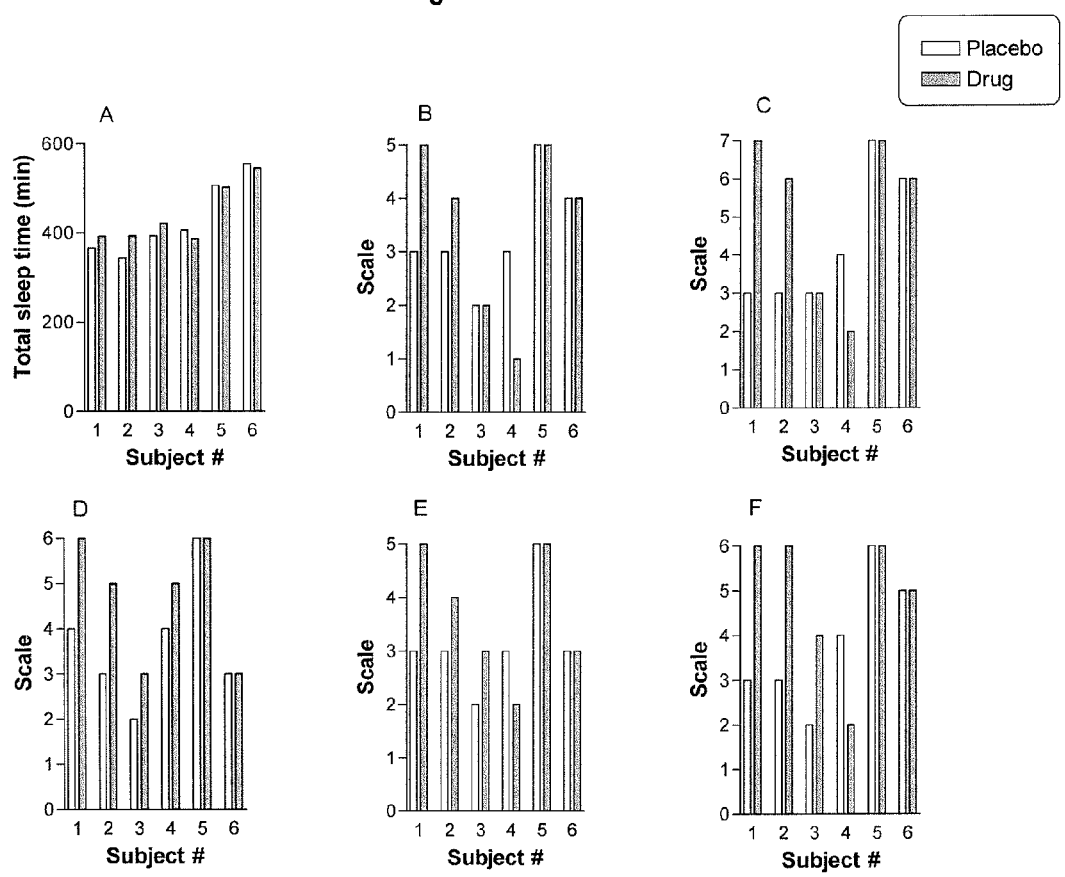
FIGS. 8A-F show (A) total sleep time of OSA patients and patients' self evaluation in response to questions (B) "How was your sleep?" (1, being very light; 5, very deep); (C) "How well did you sleep last night?" (1, very badly; 7, very well); (D) "How clear-headed did you feel this morning?" (1, very drowsy; 6, very alert); (E) "How did you feel physically after wake up?" (1, very tired; 5, very energetic); and (F) How satisfied were you with last night sleep?" (1, very unsatisfied; 6, very satisfied)

Each patient took questionnaire to self evaluate their sleep after waking up. The scores in self evaluation were compared between the placebo night and the treatment night (FIG. 8). Three patients had longer total sleep time (total sleep time until their natural wake-up) in the treatment night (average 33 min more); two patients had essentially no change in the sleep time, presumably caused by long sleep time (over 8 hours); and one patient had less sleep time because he couldn't return to sleep for minor stomach upset. Generally, patients reported better sleep, more clear-headed, more energetic, and more satisfied sleep in the treatment night, indicating that the drug improved the quality of sleep in the patients.

7) Daytime Quality of Life

Patients reported to have more energy, be more concentrated and be less sleepy during the daytime following the drug treatment night. This indicates that the drug treatment reduced daytime sleepiness, restored impaired cognitive function (e.g., impaired memory), and improved quality of life.

EXAMPLE 3

Determination of Optimum PYD Dose Range for the Treatment of OSA

The results obtained from the clinical study described in Example 1 show that the therapeutic effects of PYD did not always correlate with an increased dosage of the drug. For an example, a patient recorded lower AHI and less low $O_2$ saturation when treated with 30-60 mg PYD bromide compared with those treated with 120 mg PYD bromide (FIG. 2). This finding in the dose response is unexpected and unique.

Figure 9:
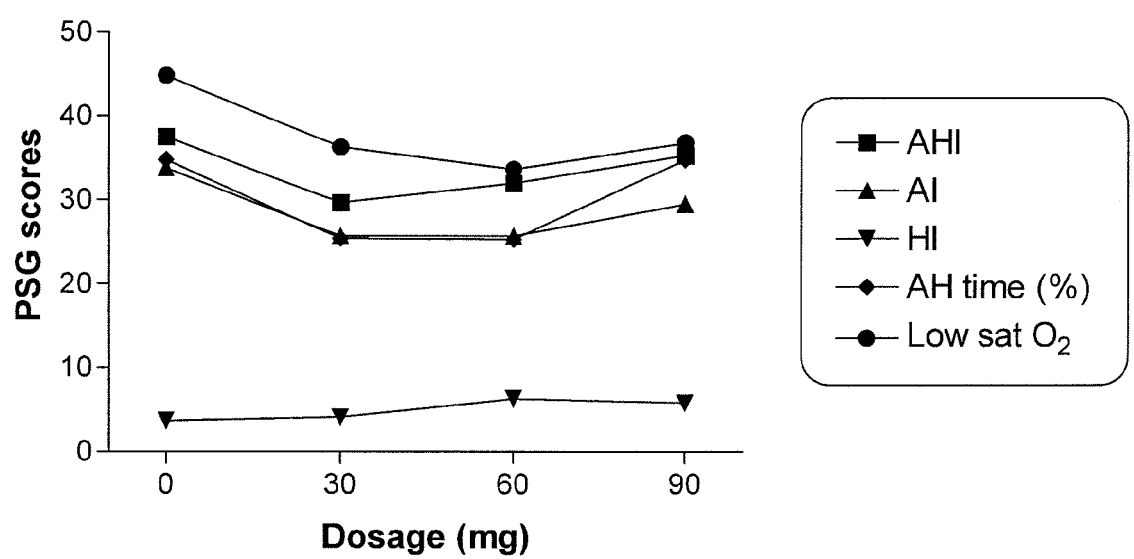
FIG. 9 shows polysomnography (PSG) scores of an OSA patient after pyridostigmine treatment.
Figure 10:
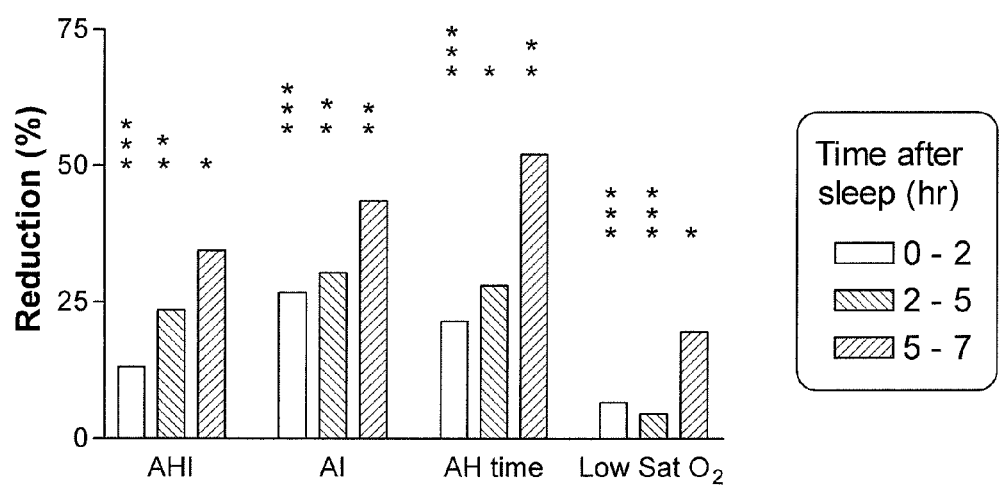
FIG. 10 shows reduction of polysomnography (PSG) scores of OSA patients after pyridostigmine treatment.

A randomized, double-blind, dose escalating study was carried out in one patient to determine optimum PYD dose range for treating OSA. The patient was administered to with 30, 60, 90 mg PYD bromide or a placebo before sleep, and was monitored by PSG throughout the night. AHI, AI, and total apnea/hypopnea time were lower in the nights administered with 30 or 60 mg PYD bromide compared with the night with 90 mg PYD bromide (FIG. 9). The number of low $O_2$ saturation events was lower with 60 mg PYD bromide compared with that of 90 mg PYD bromide. The results obtained from the clinical study described in Example 2 were reexamined to compare the therapeutic responses in the windows of 2-5 hours and 5-7 hours after sleep. PSG scores, including AHI, AI, total apnea/hypopnea time, and low $O_2$ saturation events, during 5-7 hours were statistically significantly lower than the corresponding scores during 2-5 hours (FIG. 10). Since serum PYD concentrations are expected to be lower within 5-7 hours comparing with those within 2-5 hours, the optimum dose range may be less than 90 mg of PYD bromide in a single dose.

REFERENCES

1. AASM. (2005) *International classification of sleep disorders, 2nd Edition: Diagnostic and coding manual.*, American Academy of Sleep Medicine.

2. Jean-Louis, G., Brown, C. D., Zizi, F., Ogedegbe, G., Boutin-Foster, C., Gorga, J. & McFarlane, S. I. (2010) Cardiovascular disease risk reduction with sleep apnea treatment, *Expert Rev Cardiovasc Ther.* 8, 995-1005.
3. Tregear, S., Reston, J., Schoelles, K. & Phillips, B. (2009) Obstructive sleep apnea and risk of motor vehicle crash: systematic review and meta-analysis, *J Clin Sleep Med.* 5, 573-81.
4. Epstein, L. J., Kristo, D., Strollo, P. J., Jr., Friedman, N., Malhotra, A., Patil, S. P., Ramar, K., Rogers, R., Schwab, R. J., Weaver, E. M. & Weinstein, M. D. (2009) Clinical guideline for the evaluation, management and long-term care of obstructive sleep apnea in adults, *J Clin Sleep Med.* 5, 263-76.
5. Banno, K. & Kryger, M. H. (2007) Sleep apnea: clinical investigations in humans, *Sleep Med.* 8, 400-26.
6. Young, T., Palta, M., Dempsey, J., Skatrud, J., Weber, S. & Badr, S. (1993) The occurrence of sleep-disordered breathing among middle-aged adults, *N Engl J Med.* 328, 1230-5.
7. Young, T., Peppard, P. E. & Gottlieb, D. J. (2002) Epidemiology of obstructive sleep apnea: a population health perspective, *Am J Respir Crit Care Med.* 165, 1217-39.
8. Banno, K., Walld, R. & Kryger, M. H. (2005) Increasing obesity trends in patients with sleep-disordered breathing referred to a sleep disorders center, *J Clin Sleep Med.* 1, 364-6.
9. Kushida, C. A., Littner, M. R., Morgenthaler, T., Alessi, C. A., Bailey, D., Coleman, J., Jr., Friedman, L., Hirshkowitz, M., Kapen, S., Kramer, M., Lee-Chiong, T., Loube, D. L., Owens, J., Pancer, J. P. & Wise, M. (2005) Practice parameters for the indications for polysomnography and related procedures: an update for 2005, *Sleep.* 28, 499-521.
10. Iber, C., Ancoli-Israel, S., Chesson, A. L. & Quan, S. F. (2007) *The AASM manual for the scoring of sleep and associated events: rules, terminology and technical specifications.*, American Academy of Sleep Medicine, Westchester, Ill.
11. Collop, N. A., Anderson, W. M., Boehlecke, B., Claman, D., Goldberg, R., Gottlieb, D. J., Hudgel, D., Sateia, M. & Schwab, R. (2007) Clinical guidelines for the use of unattended portable monitors in the diagnosis of obstructive sleep apnea in adult patients. Portable Monitoring Task Force of the American Academy of Sleep Medicine, *J Clin Sleep Med.* 3, 737-47.
12. Mansfield, D. R., Gollogly, N. C., Kaye, D. M., Richardson, M., Bergin, P. & Naughton, M. T. (2004) Controlled trial of continuous positive airway pressure in obstructive sleep apnea and heart failure, *Am J Respir Crit Care Med.* 169, 361-6.
13. Weaver, T. E. & Grunstein, R. R. (2008) Adherence to continuous positive airway pressure therapy: the challenge to effective treatment, *Proc Am Thorac Soc.* 5, 173-8.
14. Fleisher, K. E. & Krieger, A. C. (2007) Current trends in the treatment of obstructive sleep apnea, *J Oral Maxillofac Surg.* 65, 2056-68.
15. Hedner, J., Grote, L. & Zou, D. (2008) Pharmacological treatment of sleep apnea: current situation and future strategies, *Sleep Med Rev.* 12, 33-47.
16. Jayaraman, G., Sharafkhaneh, H., Hirshkowitz, M. & Sharafkhaneh, A. (2008) Pharmacotherapy of obstructive sleep apnea, *Ther Adv Respir Dis.* 2, 375-86.
17. Hedner, J., Kraiczi, H., Peker, Y. & Murphy, P. (2003) Reduction of sleep-disordered breathing after physostigmine, *Am J Respir Crit Care Med.* 168, 1246-51.
18. Moraes, W., Poyares, D., Sukys-Claudino, L., Guilleminault, C. & Tufik, S. (2008) Donepezil improves obstructive sleep apnea in Alzheimer disease: a double-blind, placebo-controlled study, *Chest.* 133, 677-83.
19. Aquilonius, S. M., Eckernas, S. A., Hartvig, P., Lindstrom, B. & Osterman, P. O. (1980) Pharmacokinetics and oral bioavailability of pyridostigmine in man, *Eur J Clin Pharmacol.* 18, 423-8.
20. Aquilonius, S. M., Eckernas, S. A., Hartvig, P., Lindstrom, B., Osterman, P. O. & Stalberg, E. (1983) Clinical pharmacology of pyridostigmine and neostigmine in patients with myasthenia gravis, *J Neurol Neurosurg Psychiatry.* 46, 929-35.
21. Milner-Brown, H. S., Mellenthin, M., Sharma, M. L. & Miller, R. G. (1987) Quantitative correlation between plasma pyridostigmine levels and neuromuscular function in myasthenia gravis, *Neurology.* 37, 800-3.
22. Huang, Y. T., Tsai, T. R., Cheng, C. J., Cham, T. M., Lai, T. F. & Chuo, W. H. (2007) Formulation design of an HPMC-based sustained release tablet for pyridostigmine bromide as a highly hygroscopic model drug and its in vivo/in vitro dissolution properties, *Drug Dev Ind Pharm.* 33, 1183-91.
23. Huang, Y. T., Tsai, T. R., Cheng, C. J., Cham, T. M., Lai, T. F. & Chuo, W. H. (2007) Formulation design of a highly hygroscopic drug (pyridostigmine bromide) for its hygroscopic character improvement and investigation of in vitro/in vivo dissolution properties, *Drug Dev Ind Pharm.* 33, 403-16.

What is claimed:

1. A method for treating obstructive sleep apnea (OSA) in a subject in need thereof, comprising administering to the subject an effective amount of a pharmaceutical composition comprising pyridostigmine before sleep for reducing the number of low oxygen saturation events, the total apnea/hypopnea time, or a combination thereof in the subject.

2. The method of claim 1, further comprising reducing apnea, hypopnea, snoring in the subject.

3. The method of claim 1, wherein sleep quality or daytime quality of life of the subject is improved.

4. The method of claim 1, wherein the effective amount of the pharmaceutical composition is selected to provide a target serum concentration of pyridostigmine in the subject in the range of 2-150 ng/ml for at least one hour.

5. The method of claim 1 wherein the target serum concentration is in the range of 3-60 ng/ml.

6. The method of claim 4, wherein the target serum concentration is in the range of 3-45 ng/ml.

7. The method of claim 4, wherein the target serum concentration is maintained for at least three hours.

8. The method of claim 1, wherein the pharmaceutical composition comprises 30-360 mg pyridostigmine.

9. The method of claim 1, wherein the pharmaceutical composition is administered to the subject within 2 hours before sleep.

10. The method of claim 1, wherein the pharmaceutical composition is administered to the subject in a single dose.

11. The method of claim 1, wherein the pharmaceutical composition further comprises a pharmaceutically acceptable carrier or diluent.

12. The method of claim 1, wherein the pharmaceutical composition is administered to the subject in an oral dosage form.

13. The method of claim 12, wherein the pharmaceutical composition is administered to the subject for gastrointestinal adsorption.

14. The method of claim 1, wherein the pharmaceutical composition is administered to the subject in a dosage form for controlled release of pyridostigmine.

15. The method of claim 1, further comprising providing the subject a mechanical treatment.

16. The method of claim 15, wherein the mechanical treatment comprises the use of continuous positive airway pressure (CPAP) devices, mandibular repositioning appliances (MRA) or tongue retaining devices.

17. The method of claim 1, further comprising administering to the subject an effective amount of a deep sleep promoting agent.

18. The method of claim 1, further comprising reducing the apnea index in the subject.

19. The method of claim 1, wherein the number of low oxygen saturation events in the subject is reduced.

20. The method of claim 1, wherein the total apnea/hypopnea time in this subject is reduced.

* * * * *